US008895726B2

(12) United States Patent
Lejeune et al.

(10) Patent No.: US 8,895,726 B2
(45) Date of Patent: Nov. 25, 2014

(54) COMPOUNDS DERIVED FROM INDOLE AND PHARMACEUTICAL COMPOSITIONS CONTAINING THEM

(75) Inventors: Fabrice Lejeune, Tourcoing (FR); Jamal Tazi, Clapiers (FR); David Grierson, Vancouver (CA); Christian Rivalle, Paris (FR); Florence Mahuteau-Betzer, Saint-Remy-les-Chevreuse (FR)

(73) Assignees: The Institut Curie, Paris (FR); The University of Montpellier 2 Science and Techniques, Montpellier (FR)

( * ) Notice: Subject to any disclaimer, the term of this patent is extended or adjusted under 35 U.S.C. 154(b) by 801 days.

(21) Appl. No.: 12/527,071

(22) PCT Filed: Feb. 19, 2008

(86) PCT No.: PCT/EP2008/052025
§ 371 (c)(1),
(2), (4) Date: Feb. 16, 2010

(87) PCT Pub. No.: WO2008/101935
PCT Pub. Date: Aug. 28, 2008

(65) Prior Publication Data
US 2011/0003843 A1  Jan. 6, 2011

(30) Foreign Application Priority Data

Feb. 19, 2007  (FR) ...................................... 07 53349
Mar. 21, 2007  (FR) ...................................... 07 53975

(51) Int. Cl.
| | | |
|---|---|---|
| *C07D 345/00* | (2006.01) | |
| *C07D 517/00* | (2006.01) | |
| *C07D 471/04* | (2006.01) | |
| *C07D 471/14* | (2006.01) | |
| *C07D 401/12* | (2006.01) | |

(52) U.S. Cl.
CPC ............ *C07D 471/14* (2013.01); *C07D 471/04* (2013.01); *C07D 401/12* (2013.01)
USPC ............... 540/1; 514/287; 514/309; 514/285; 546/141; 546/64; 546/70

(58) Field of Classification Search
USPC ............... 514/287, 309, 285; 546/141, 64, 70
See application file for complete search history.

(56) References Cited

U.S. PATENT DOCUMENTS 5,977,164 A * 11/1999 Carver et al. ................. 514/449

FOREIGN PATENT DOCUMENTS

WO  WO 2005/023255  3/2005

OTHER PUBLICATIONS

STN Accession No. 1981:587113 CAPLUS.*
Patani "Bioisosterism: A rational Apprpach in drug design", Chem. Rev. 1996, 96 (8) 3147-3176.*
International Search Report issued Dec. 2, 2008 in application No. PCT/EP2008/052025.
Balkau et al., *Australian Journal of Chemistry*, vol. 22, pp. 2489-2492, 1969.
Bashkirov et al., "A mouse sytoplasmic exoribonuclease (mXRN1p) with preference for G4 tetraplex substrates," *J. Cell Biol.*, vol. 136, pp. 761-773, 1997.
Belgrader et al., "Nonsense but not missence mutations can decrease the abundance of nuclear mRNA for the mouse major urinary protein, while both types of mutations can facilitate exon skipping," *Mol. Cell Biol.*, vol. 14, pp. 6326-6336, 1994.
Brengues et al., "Movement of eukaryotic mRNAs between polysomes and cytoplasmic processing bodies," *Science*, vol. 310, pp. 486-489, 2005.
Bisagni et al., *Heterocycles*, vol. 27, pp. 1671-1678, 1988.
Buu-Hoi et al., "Carcinogenic nitrogen compounds Part LVI: Benzcacridines and benzoacarbazoles methylated on the K-Zone," *Journal of the Chemical Society*, pp. 662-665, 1967.

(Continued)

*Primary Examiner* — Wu-Cheng Winston Shen
*Assistant Examiner* — Jean Cornet
(74) *Attorney, Agent, or Firm* — Oliff PLC

(57) ABSTRACT

The present invention relates to a compound derived from indole corresponding to the following formula II:

Formula II wherein X represents N, CR8 or $N^+R8$, wherein R8 represents a hydrogen atom, a hydroxyl or alkyl or methoxy group optionally substituted with a phenyl group; R2, R3 and R4 independently represent a hydrogen atom or a halogen atom or an optionally substituted alkyl, amine, alkene, ester, sulfonamide, ether or benzyl group; R5 represents a hydrogen atom or an optionally substituted, saturated or unsaturated alkyl group, amine, benzyl group; R6 represents an optionally substituted C1-C3 alkyl group; R7 represents a hydrogen atom or an optionally substituted C1-C3 alkyl group and R7 is absent when the ring A is in the b position, and A represents a ring; R9 and R10 represent together a carbon bond or independently represent an R11 OR11, SR11 group; wherein R11 represents a hydrogen atom, an optionally substituted, saturated or unsaturated, C1-C3 alkyl group, which may contain one or more sulfur, oxygen or nitrogen atoms; pharmaceutically acceptable salts of said compounds, their isomers and/or a mixture thereof; pharmaceutical composition comprising such a compound; the use of such a compound for preparing a drug intended to treat a genetic disease resulting from at least one mutation causing the occurrence of an early termination codon.

19 Claims, No Drawings

(56) References Cited

OTHER PUBLICATIONS

Carvalho et al., "Investigation of geometry and some electronica properties of aza analogues of the ellipticine and olivacine derivatives," *Theochem*, vol. 539, pp. 273-278, 2001.
Chen et al., "Rapid deadenylation triggered by a nonsense codon precedes decay of the RNA body in a mammalian cytoplasmic nonsense-mediated decay pathway," *Mol. Cell Biol.*, vol. 23, pp. 4805-4813, 2003.
Chiu et al., "Characterization of human Smg5/7a: a protein with similarities to *Caenorhabditis elegans* SMG5 and SMG7 that functions in the dephosphorylation of Upf1," *Rna.*, vol. 9, pp. 77-87, 2003.
Conti et al., "Nonsense-mediated mRNA decay: molecular insights and mechanistic variations across species," *Curr. Opin. Cell Biol.*, vol. 17, pp. 316-325, 2005.
Cougot et al., "Cytoplasmic foci are sites of mRNA decay in human cells," *J. Cell Biol.*, vol. 165, pp. 31-40, 2004.
Couttet et al., "Premature termination codons enhance mRNA decapping in human cells," *Nucleic Acids Res.*, vol. 32, pp. 488-494, 2004.
Czaplinski et al., "The surveillance complex interacts with the translation release factors to enhance termination and degrade aberrant mRNA's," *Genes Dev.*, vol. 12, pp. 1665-1677, 1998.
Ducrocq et al., *Tetrahedron*, vol. 35, pp. 142-145, 1979.
Fenger-Gron et al., "Multiple processing body factors and the ARE binding protein TTP activate mRNA decapping," *Mol. Cell*, vol. 20, pp. 905-915, 2005.
Fukuhara et al., "SMG7 is a 14-3-3-like adaptor in the nonsense-mediated mRNA decay pathway," *Mol. Cell*, vol. 17, pp. 537-547, 2005.
Fusco et al., "Single mRNA molecules demonstrate probabilistic movement in living mammalian cells," *Curr. Biol.*, vol. 13, pp. 161-170, 2003.
Frischmeyer et al., "Nonsense-mediated mRNA decay in health and disease," *Human Molecular Genetics*, vol. 8, No. 10, pp. 1893-1900, 1999.
Gehring et al., "Exon-junction complex components specify distinct routes of nonsense-mediated mRNA decay with differential cofactor requirements," *Mol. Cell*, vol. 20, pp. 65-75, 2005.
He et al., "Genome-wide analysis of mRNAs regulated by the nonsense-mediated and 5' to 3' mRNA decay pathways in yeast," *Mol. Cell*, vol. 12, pp. 1439-1452, 2003.
Hosoda et al., "CBP80 promotes interaction of Upf1 with Upf2 during nonsense-mediated and mRNA decay in mammalian cells," *Nat. Struct. Mol. Biol.*, vol. 12, pp. 893-901, 2005.
Ingelfinger et al., The human LSml-7 proteins colcalize with the mRNA-degrading enzymes Dep1/2 and Xrnl in distinet cytoplasmic foci, *Rna*, vol. 8, pp. 1489-1501, 2002.
Ishigaki et al., "Evidence for a pioneer round of mRNA translation: MRNAs subject to nonsense-mediated decay in mammalian cells are bound by CBP80 and CBP20," *Cell*, vol. 106, pp. 607-617, 2001.
Kansal et al., "The biogenetic synthetic and biochemical aspects of ellipticine an antitumor alkaloid," *Tetrahedron*, vol. 42, No. 9, pp. 2389-2408, 1986.
Kashima et al., "Binding of a novel SMG-1-Upf1-eRF1-eRF3 complex (SURF) to the exon junction comples triggers Upf1 phosphorylation and nonsense-mediated mRNA decay," *Genes Dev.*, vol. 20, pp. 355-367, 2006.
Kedersha et al., "Stress granules and processing bodies are dynamically linked sites of mRNP remodeling," *J. Cell Biol.*, vol. 169, pp. 871-884, 2005.
Kim et al., "Mammalian Staufen1 recruits Upf1 to specific mRNA 3'UTRs so as to elicit mRNA decay," *Cell*, vol. 120, pp. 195-208, 2005.
Kuzmiak et al., "Applying nonsense-mediated mRNA decay research to the clinic: progress and challenges," *Trends Mol., Med.*, 2006.
Lejune et al., "Nonsense-mediated mRNA decay in mammalian cells involves decapping deadenylating and exonuclcolytic activities," *Mol. Cell.*, vol. 12, pp. 675-687, 2003.

Lejune et al., "Immunopurification and analysis of protein and RNA components of mRNP in mammalian cells," *Methods Mol. Biol.*, vol. 257, pp. 115-124, 2004.
Lejune et al., "Mechanistic links between nonsense-mediated mRNA decay and pre-mRNA splicing in mammalian cells," *Curr. Opin. Cell Biol.*, vol. 17, pp. 309-315, 2005.
Lykke-Andersen et al., "Human Upf proteins target an MRNA for nonsense-mediated decay when bound downstream of a termination codon," *Cell*, vol. 103, pp. 1121-1131, 2000.
Maquat, "Nonsense-Mediated mRNA Decay: A Comparative Analysis of Difference Species," *Current Genomics*, vol. 5, pp. 175-190, 2004.
Maquat, "Nonsense-mediated mRNA decay: splicing, translation and MRNP dynamics," *Nat. Rev. Mol Cell Biol*, vol. 5, pp. 89-99, 2004.
Mendell et al., "Separable roles for rent1/hUpf1 in altered splicing and decay of nonsense transcripts," *Science*, vol. 298, pp. 419-422, 2002.
Mendell et al., "Nonsense surveillance regulates expression of diverse classes of mammalian transcripts and mutes genomic noise," *Nat. Genet.*, vol. 36, pp. 1073-1078, 2004.
Miller et al., "Total synthesis of ellipticine and 9-methoxyellipticine via benzotriazole intermediates," *Journal of Organic Chemistry*, vol. 48, No. 6, pp. 886-888, 1983.
Miller et al., "A general synthesis of 6H-pyrido[4,3-b]carbazole alkaloids," *Tetrahedron Letters*, vol. 21, No. 35, pp. 3319-3322, 1980.
Moriarty et al., "Selenium deficiency reduces the abundance of mRNA for Se-dependent glutathione peroxidase 1 by a UGA-dependent mechanism likely to be nonsense codon-mediated decay of cytoplasmic mRNA," *Mol. Cell Biol.*, vol. 18, pp. 2932-2939, 1998.
Ohashi et al., "Ellipticine and related anti-cancer agents," *Expert Opinion on Therapeutic Patents*, vol. 6, No. 12, pp. 1285-1294, 1996.
Ohnishi et al., "Phosphorylation of hUPPF1 induces formation of mRNA surveillance complexes containing hSMA-5 and hSMG-7," *Mol. Cell*, vol. 12, pp. 1187-1200, 2003.
Page et al., "SMG-2 is a phosphorylated protein required for mRNA surveillance in *Caenorhabditis elegans* and related to Upflp of yeast," *Mol. Cell Biol.*, vol. 19, pp. 5943-5941, 1999.
Pal et al., "Evidence that phosphorylation of human Upf1 portein varies with intracellular location and is medated by a wortmannin-senstive and rapamycin-sensitive PI 3-kinase-related kinase signaling pathway," *Rna*, vol. 7, pp. 5-15, 2001.
Pillai et al., "Inhibition of translation initiation by Let-7 MicroRNA in human cells," *Science*, vol. 309, pp. 1573-1576, 2005.
Rehwinkel et al., "Nonsense-mediated mRNA decay factors act in concert to regulate common mRNA targets," *Rna*, vol. 11, pp. 1530-1544.
Rivalle et al., *J. Med. Chem.*, vol. 26, pp. 181-185, 1983.
Rivalle et al., "11H-Pyrido[3', 2': 4,5]pyrrolo[2,3-g]isoquinolines (7-azaellipticines) substituted at postion 6"," *Tetrahedron*, vol. 37, No. 11, pp. 2097-2103, 1981.
Schenkmann et al., "Structure-activity relationships of mammalian topoisomerase II inhibitors related to ellipticine," *Database CA [Online] Chemical Abstracts Service*, Database accession No. 1993:32514, RN=145204-43-9, abstract, 1992.
Serin et al., "Identification and characterization of human orthologues to *Saccharomyces cerevisiae* Upf2 protein and Upf3 protein (*Caenorhabditis elegans* SMG-4)," *Mol. Cell Biol.*, vol. 21, pp. 209-223, 2001.
Sheth et al., "Decapping and decay of messenger RNA occur in cytoplasmic processing bodies," *Science*, vol. 300, pp. 805-808, 2003.
Sheth et al., "Targeting of aberrant mRNAs to cytoplasmic processing bodies," *Cell*, vol. 125, pp. 1095-1109, 2006.
Soret et al., "Selective modification of alternative splicing by indole derivatives that target serine-arginine-rich protein splicing factors," *Proc. Natl. Acad. Sci USA*, vol. 102, pp. 8764-8769, 2005.
Sun et al., "A mutated human homologue to years Upf1 protein has a dominant-negative effect on the decay of nonsense-containing mRNAs in mammalian cells," *Proc. Natl. Acad. Sci. USA*, vol. 95, pp. 10009-10014, 1998.

(56) References Cited

OTHER PUBLICATIONS

Sureau et al., "SC35 autoregulates its expression by promoting splicing events that destabilize its mRNAs," *Embo. J.*, vol. 20, pp. 1785-1796, 2001.

Teixeira et al., "Processing bodies require RNA for assembly and contain nontranslating mRNAs," *Rna*, vol. 11, pp. 371-382, 2005.

Tsuchimoto et al., "Easy access to aryl- and heteroaryl-annulated[a]carbazoles by the induium-catalyzed reaction of 2-arylindoles with propargyl ethers," *Angew. Chem, Int. Ed.*, vol. 44, pp. 1336-1340, 2005.

Thermann et al., "Binary specification of nonsense codons by splicing and cytoplasmic translation," *Embo J.*, vol. 17, pp. 3484-3494, 1998.

Tourriere et al., "The RasGAP-associated endoribonuclease G3BP assembles stress granules," *J. Cell Biol.*, vol. 160, pp. 823-831, 2003.

Unterholzner et al., "SMG7 acts as a molecular link between mRNA surveillance and mRNA decay," *Mol. Cell.*, vol. 16, pp. 587-596, 2004.

Van Dijk et al., "Human Dcp2: a catalytically active mRNA decapping enzyme located in specific cytoplasmic structures," *Embo. J*, vol. 21, pp. 6915-6924, 2002.

Vendome et al., "Molecular Modeling of Wild-Type and D816V c-Kit Inhibition Based on ATP-Competitive Binding of Ellipticine Derivatives to Tyrosine Kinases," *Journal of Medicinal Chemistry*, vol. 48, No. 20, pp. 6194-6201, 2005.

Vernon et al., "Naphthalen-1,4-imine derivatives with bridgehead substituents," *Database CA [Online] Chemical Abstracts Service*, Database accession No. 1977:484708, RN=892-37-5, abstract, 1977.

Wollerton et al., "Autoregulation of polypyrimidine tract binding protein by alternative splicing leading to nonsense-mediated decay," *Mol Cell*, vol. 13, pp. 91-100, 2004.

Wolthius et al., "Reactions of benzyne with pyrroles," *Journal of Organic Chemistry*, vol. 30, No. 1, pp. 190-193, 1965.

Yamashita et al., "Human SMG-1, a novel phosphatidylinositol 3-kinase-related protein kinase, associates with components of the mRNA surveillance complex and is involved in the regulation of nonsense-mediated mRNA decay," *Genes Dev.*, vol. 15, pp. 2215-2228, 2001.

Yu et al., "Ge-1 is a central component of the mammalian cytoplasmic mRNA processing body," *Rna*, vol. 11, pp. 1795-1802, 2005.

Zhang et al., "Intron function in the nonsense-mediated decay of beta-globin mRNA: indications that pre-mRNA splicing in the nucleus can influence mRNA translation in the cytoplasm," *Rna*, vol. 4, pp. 801-815, 1998.

\* cited by examiner

COMPOUNDS DERIVED FROM INDOLE AND PHARMACEUTICAL COMPOSITIONS CONTAINING THEM

The degradation process of mRNAs having an early stop codon (Nonsense-Mediated mRNA Decay, NMD) is a qualitative control process identified in all eukaryotic organisms studied to this day (CONTI and IZAURRALDE, 2005; MAQUAT, 2004a). One of the roles of this mechanism is to degrade mRNAs having a premature termination codon (PTC) so as to prevent synthesis of truncated proteins which would not be functional or the function of which might be deleterious for the cell. Further, the NMD route was identified as being involved in gene regulation in yeasts, in drosophilae and mammals (HE et al., 2003; MENDELL et al., 2002; REHWINKEL et al., 2005; SUREAU et al., 2001; WOLLERTON et al., 2004).

In mammal cells, NMD takes place after the splicing of pre-messenger RNAs and is, in most cases, modulated by a protein complex of 20-24 nucleotides fixed upstream from the exon-exon junction (Conti and Izaurralde, 2005; Lejeune and Maquat, 2005; Maquat, 2004b). This protein complex, called exon-junction complex, EJC, is supposed to recruit the retained UPF proteins which play an essential role, non-characterized to this day, in NMD. During what is called the <<first translation cycle>> (Ishigaki et al., 2001), the PTCs are recognized and the targeted mRNAs are degraded by a digestion 5' towards 3', involving removal of the cap and of exoribonucleases such as hXRN1 and hXRN2/hRAT1, and by digestion 3' towards 5' involving deadenylation and the exosome (Chen and Shyu, 2003; Couttet and Grange, 2004; Lejeune et al., 2003).

UPF1 is a phosphoprotein which undergoes a phosphorylation/dephosphorylation cycle during NMD (Ohnishi et al., 2003; Page et al., 1999; Pal et al., 2001). It was demonstrated that UPF1 interacts with translation termination factors in yeasts (Czaplinski et al., 1998) and in mammals (Kashima et al., 2006), and may therefore be the connection between EJC and the translation termination complex. Direct interaction between hUPF1 and the cap-binding protein CBP80 was recently demonstrated in mammal cells (Hosoda et al., 2005), indicating that hUPF1 establishes a complex interaction before or during the first translation cycle. It was demonstrated that phosphorylation of the hUPF1 is carried out by hSMG1, a kinase related to PI3 (Page et al., 1999; Pal et al., 2001; Yamashita et al., 2001), and requires the presence of hUPF2 and hUPF3 (Kashima et al., 2006) By contrast, dephosphorylation of hUPF1 requires the presence of a multiprotein complex composed of hSMG5, hSMG6, hSMG7 and of (PP)-2A phosphatase protein (Chiu et al., 2003; Ohnishi et al., 2003). The hSMG5 and hSMG7 proteins are mainly localized in the cytoplasm, a fraction of which is present in the processing bodies (P-bodies) (Unterholzner and Izaurralde, 2004). hSMG6 is also a cytoplasmic protein which is concentrated in certain cytoplasmic foci which seem to be distinct from P-bodies and for which the nature is still undetermined (Unterholzner and Izaurralde, 2004).

<<P-bodies>> have been described in higher and lower eukaryotic cells (Cougot et al., 2004; Sheth and Parker, 2003). In mammals, these cytoplasmic structures contain multiple factors involved in the degradation of mRNAs including components of the mechanism for removing the cap, such as DCP1a (Ingelfinger et al., 2002), DCP2 (Ingelfinger et al., 2002; van Dijk et al., 2002), GE1 (Yu et al., 2005) also called HEDLS (Fenger-Gron et al., 2005), p54/RCK (Cougot et al., 2004), deadenylase CCR4 (Cougot et al., 2004), XRN1 (Bashkirov et al., 1997), the LSM1-7 complex involved in different aspects of the processes related to RNA (Cougot et al., 2004; Ingelfinger et al., 2002), and the components of the NMD machinery which are hUPF1, hSMG5 and hSMG7 (Fukuhara et al., 2005; Unterholzner and Izaurralde, 2004). The function of the P-bodies is still indeterminate but they may be used as a storage compartment for non-translated mRNAs and for proteins involved in the degradation of mRNAs (Brengues et al., 2005; Pillai et al., 2005; Teixeira et al., 2005), and/or in the degradation site of RNAs (Cougot et al., 2004; Sheth and Parker, 2006).

Today, nearly one third of human genetic diseases would originate from the occurrence of an early stop codon (Frischmeyer and Dietz, 1999; Kuzmiak and Maquat, 2006). In the large majority of cases, the stop codon causes degradation of the mRNA which bears it, by the NMD mechanism. The result is then absence of expression of the relevant gene and this even when the mutation in question would allow translation of a functional truncated protein. By inhibiting the NMD mechanism in patients affected by such pathologies, it would be possible to restore expression of the functional truncated protein and as such this is an interesting lead.

The inventors have shown that particular indole derivatives were capable of specifically inhibiting NMD in vitro and in vivo, and that said compounds allowed an increase in the expression level of the mRNA of dystrophin having premature stop codons in cell lines from patients affected with Duchenne's muscular dystrophy (DMD).

Accordingly, a first object of the invention relates to compounds derived from indole corresponding to the following formula II:

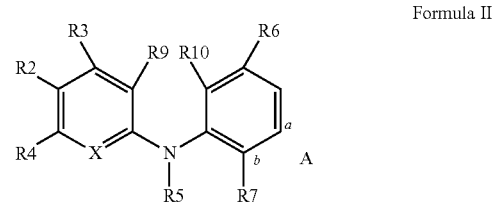

Formula II wherein:

X represents N, CR8 or the anhydrobase $N^+R8$, wherein R8 represents a hydrogen atom, a hydroxyl or alkyl or methoxy group optionally substituted with a phenyl group, preferably R8 represents a hydrogen atom, R2, R3 and R4 independently represent a hydrogen atom or a halogen atom or an optionally substituted alkyl, amine, alkene, ester, sulfonamide, ether group, such as a methoxy or trifluoromethoxy, or benzyl group, R5 represents a hydrogen atom or an optionally substituted saturated or unsaturated alkyl group, amine, benzyl group, R6 represents an optionally substituted C1-C3 alkyl group, preferably a methyl or ethyl group, and more preferably R6 represents a methyl group, R7 represents a hydrogen atom or an optionally substituted C1-C3 alkyl group and R7 is absent when the ring A is in the b position, and R9 and R10 represent together a carbon bond or independently represent a hydrogen atom, a R11, OR11, SR11, NR11R12 group, wherein R11 and R12 independently represent a hydrogen atom, an oxygen atom, an optionally substituted saturated or unsaturated, C1-C3 alkyl group, which may contain one or more sulfur, oxygen or nitrogen atoms. Preferably, when R11 and/or R12 represent a substituted alkyl group, the alkyl group is substituted with a halogen, preferably fluorine.

A represents a ring which, when A is in the a or b position, corresponds to

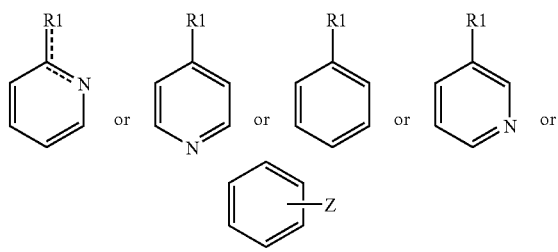

wherein:

R1 represents a hydrogen, oxygen or halogen atom, or an optionally substituted, linear or branched and/or unsaturated alkyl or amine group, and Z represents a R1 group;

pharmaceutically acceptable salts of said compounds, their isomers and/or mixture thereof.

By <<halogen atom>> is meant the group F, Cl, Br and I, and more particularly Cl.

By <<unsaturated alkyl group>> is meant an alkyl group having at least one double bond.

Advantageously X represents N or the anhydrobase $N^+R8$.

In the case when X represents the anhydrobase $N^+R8$ and when R5 represents a hydrogen, there is an equilibrium between the two following forms:

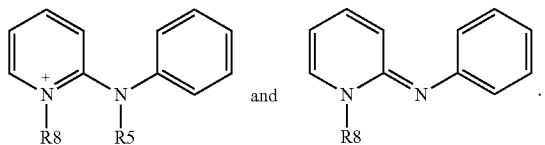

Advantageously, R2, R3 and R4 represent independently of each other, a hydrogen atom or a halogen atom or an optionally substituted alkyl, amine, alkene or benzyl group.

Still advantageously, R2, R3 and R4 represent independently of each other, a hydrogen atom or a halogen atom or a C1-C4 alkyl group, and preferably, R2, R3 and R4 represent a hydrogen atom.

Preferably, R2, R3 and/or R4 represent independently of each other a halogen atom selected from the group comprising F, Cl, Br and I, preferably said halogen atom is a Cl atom.

Advantageously, R5 represents a hydrogen atom or a saturated or unsaturated alkyl group such as a methyl, ethyl, propyl or butyl group, and more preferably, R5 represents a hydrogen atom.

Advantageously, R7 represents a methyl or ethyl group, and more preferably R7 represents a methyl group.

Advantageously, R1 is a hydrogen, oxygen or halogen atom.

Advantageously, R9 and R10 represent independently of each other a hydrogen atom, a R11, OR11 or SR11 group.

In a first particular embodiment, when R9 represents a group different from a hydrogen atom, then R10 represents a hydrogen atom.

Advantageously, R9 represents an OR11 group, wherein R11 represents a hydrogen atom, a optionally substituted, saturated or unsaturated C1-C3 alkyl group, which may contain one or more sulfur, oxygen or nitrogen atoms, preferably a methyl group.

Preferably, the compound of formula I fits the following formula:

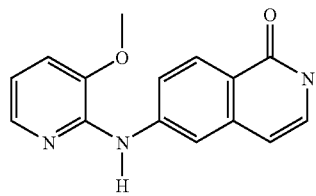 [SMILES: COc1cccnc1Nc1ccc2c(=O)[nH]ccc2c1]

In a second particular embodiment, when R10 represents a group different from a hydrogen atom, then R9 represents a hydrogen atom.

Advantageously, R9 and R10 both represent a hydrogen atom. The compound of general formula II then fits the following formula Ia:

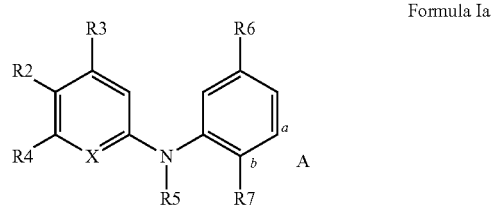

Formula Ia wherein R2, R3, R4, R5, R6, R7, X and the ring A are as defined earlier.

A preferred compound of formula Ia is 5,8-dimethyl-6(5-methyl-pyridin-2-ylamine)-isoquinoline.

Another preferred compound of formula Ia is 5,8-dimethyl-6-(pyridin-2-ylamino)-2H-isoquinolin-1-one.

Preferably, R9 and R10 represent a hydrogen, and X represents N or the anhydrobase $N^{30}$ R8.

In a third particular embodiment, R9 and R10 represent together a carbon bond, the compound of general formula II then fitting the following formula Ib:

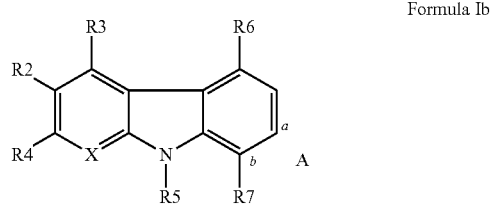

Formula Ib wherein R2, R3, R4, R5, R6, R7, X and the ring A are as defined earlier.

Still advantageously, the ring A is in the a position.

In a fourth particular embodiment, the ring A represents

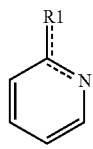

wherein R1 represents a hydrogen, oxygen or halogen atom, or an optionally substituted, linear or branched and/or unsaturated alkyl or amine group, When the ring A has the following formula:

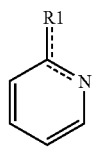

it may indifferently represent a group

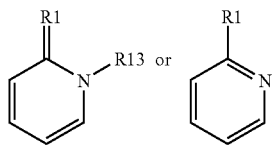

wherein R13 represents a hydrogen atom or an optionally substituted C1-C4 alkyl group and R1 is as defined earlier.

Advantageously, the ring A represents the group:

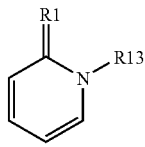

wherein R1 represents an oxygen atom, an amine group or an optionally substituted, linear or branched and/or unsaturated alkyl group and R13 represents an optionally substituted C1-C4 alkyl group.

Still advantageously, the ring A represents the group:

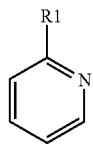

wherein R1 represents a hydrogen, oxygen or halogen atom, or an optionally substituted, linear or branched and/or unsaturated alkyl or amine group, preferably a hydrogen atom or a halogen, preferably a chlorine atom.

In another preferential embodiment, A is selected from the group comprising:

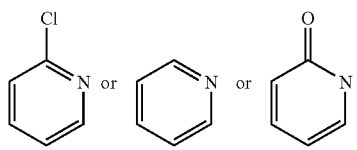

In an embodiment according to the invention, the compounds derived from indole of formula II fit the following formula I:

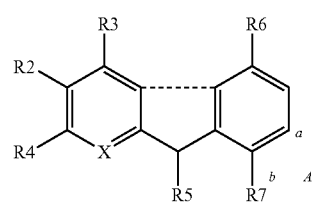

Formula I wherein R2, R3, R4, R5, R6, R7, X and the ring A are as defined earlier;

X, R1, R2, R3, R4, R5, R6, R7 and the ring A are as defined earlier;

pharmaceutically acceptable salts of said compounds, their isomers and/or mixture thereof.

By formula I, are designated compounds of formula:

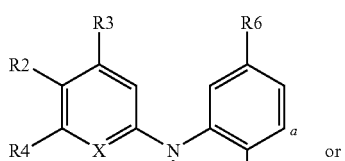

Ia

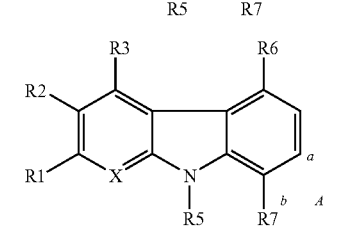

Ib

According to another preferential embodiment, the compounds derived from indole are selected from the group comprising:
- 6-chloro-5,10-dimethyl-11H-pyrido[3',2':4,5]pyrrolo[3,2-g]isoquinoline (compound 70);
- 5,10-dimethyl-11H-pyrido[3',2':4,5]pyrrolo[3,2-g]isoquinoline (compound 71);
- 5,8-dimethyl-6-(pyridin-2-ylamino)-2H-isoquinolin-1-one; (compound 72);
- 5,8-dimethyl-6-(3-methoxy-pyridin-2-ylamino)-isoquinolin-1-one (compound 497); and
- 5,8-dimethyl-6(5-methyl-pyridin-2-ylamino)-isoquinoline (compound 500).

Preferably, the compound derived from indole is selected from the group consisting of 5,8-dimethyl-6-(pyridin-2- ylamino)-2H-isoquinolin-1-one, 5,8-dimethyl 6-(3-methoxy-pyridin-2-ylamino)-isoquinolin-1-one and 5,8-dimethyl-6-(5-methyl-pyridin-2-ylamino)-isoquinoline.

Advantageously, the compound derived from indole is 5,8-dimethyl-6-(pyridin-2-ylamino)-2H-isoquinolin-1-one.

A second object of the invention consists in a pharmaceutical composition comprising at least one indole derivative as described earlier and optionally a pharmaceutically acceptable support.

As an example of pharmaceutically acceptable support, the composition may comprise emulsions, micro-emulsions, oil-in-water emulsions, anhydrous lipids and water-in-oil emulsions, or other types of emulsions.

The composition according to the invention may further comprise one or more additives such as diluents, excipients, stabilizers and preservatives. Such additives are well-known to one skilled in the art, and notably described in <<Ullmann's Encyclopedia of Industrial Chemistry, 6$^{th}$ Ed. >> (different editors, 1989-1998, Marcel Dekker); and in <<Pharmaceutical Dosage Forms and Drug Delivery Systems>> (ANSEL et al., 1994, WILLIAMS & WILKINS).

A third object consists in the use of at least one indole derivative, as described earlier, for preparing a drug intended to treat, in a subject, a genetic disease resulting from at least one mutation causing the occurrence of an early termination codon.

As used in the present application, the term of <<subject>> corresponds to a mammal such as rodent, a felid, a canid, a primate or a human, preferably said subject is a human.

Such genetic diseases resulting from at least one mutation causing the occurrence of an early termination codon are well-known and would account for nearly one third of genetic diseases presently. As an example of such genetic diseases, mention may be made of β-thalassemia, Marfan's syndrome, Duchenne's muscular dystrophy (DMD), Becker's muscular dystrophy (DMD), Ullrich's disease, Hurler's syndrome or cystic fibrosis (CF), better known under the name of mucoviscidosis, and for subjects having a premature termination codon in the involved gene in said genetic diseases.

Preferably, with said mutation after all, a functional truncated protein may be obtained.

The compounds according to the invention actually have the capacity of inhibiting the NMD mechanism and of allowing translation of mRNA having premature termination codons.

By functional protein is meant a protein allowing restoration of a wild phenotype.

Advantageously, by <<functional protein>> is meant a protein having sufficient activity relatively to the wild protein for providing the same function as the latter and allowing a wild phenotype to be obtained.

A fourth object of the invention deals with a method for therapeutic treatment of a subject for a genetic disease resulting from at least one mutation causing the occurrence of an early termination codon, comprising the administration of a therapeutically effective amount of a pharmaceutical composition as described earlier.

By <<therapeutically effective amount>> is meant an amount with which inhibition of NMD may be induced. One skilled in the art will be able to determine said therapeutically effective amount in the light of his general knowledge and of the methods described in the examples.

The compounds will be able to be administered with any administration mode, for example via an intramuscular, intravenous, oral route, etc.

The examples which follow are provided as an illustration and cannot limit the scope of the present invention.

EXAMPLES

I-Material and Methods
I-1 Indole Compounds

All the polycyclic indole compounds used were suspended in DMSO at 20 mg/mL, and then prepared to a dilution of 5 mM in 10% (v/v) DMSO.

The tested compounds are shown in the following Table I:

TABLE I

| Compounds | Formula | Nomeclature |
|---|---|---|
| 13 | | N-(5,6-Dimethyl-5H-pyrido[3',4';4,5]pyrrolo-[2,3-g]isoquinolin-10-yl)N'-ethyl-propan-1,3-diamine |
| 15 | | N'-(5,6-Dimethyl-5H-pyrido[3',4';4, 5]pyrrolo-[2,3-g]isoquinolin-10-yl)N,N-diethyl-propane-1,3-diamine |

| Compounds | Formula | Nomenclature |
|---|---|---|
| 17 | | 1-(3-Diethylamino-propylamino)-5-methyl-6H-pyrido[4,3-b]carbazol-9-ol |
| 29 | | 1-Chloro-2,6-dimeethyl-2H-pyrido[3',4';4,5]-pyrrolo[2,3-g]isoquinoline |
| 35 | | 1-(3-Dimethylamino-propylamino)-5-methyl-6H-pyrido[4,3-b]carbazol-9-ol |
| 37 | | N'-(5,6-Dimethyl-5H-pyrido[3',4';4,5]pyrrolo[2,3g]isoquinolin-10-yl)-N,N-dimethyl-propane-1,3-diamine |
| 39 | | N,N-Dieethyl-N'-(9-methoxy-5,6-dimethyl-6H-pyrido[4,3-b[carbazol-1-yl)-ethane-1,2-diamine |
| 67 | | 6-Chloro-1-methyl-11H-pyrid[3',2':4,5]-pyrrolo[3,2-g]isoquinoline |

TABLE I-continued

| Compounds | Formula | Nomeclature |
|---|---|---|
| 70 | | 6-Chloro-5,1-0dimethyl-11H-pyrido[3',2':4,5]-pyrrolo[3,2-g]isoquinoline |
| 71 | | 5,10-dimethyl-11H-pyrido[3',2':4,5]-pyrrolo[3,2-g]isoquinoline |
| 72 | | 5,8-Dimethyl-6-(pyridin-2-ylamino)-2H-isoquinolin-1-one |
| 81 | | Allyl-(9-methoxy-5,11-dimethyl-6H-pyrido[4,3-b]carbazol-1-yl)-amine |
| 497 | | 5,8-dimethyl-6-(3-methoxy-pyridin-2-ylamino)-isoquinolin-1-one |
| 500 | | 5,8-dimethyl-6-(5-methyl-pyridin-2-ylamino) isoquinoline |

I-3 Synthesis of the Compounds According to the Present Invention

The synthesis of compounds 17, 35 and 39 is described in the following publication: RIVALLE et al., *J. Med. Chem.* 1983, 26, 181-185.

The compound 81 is obtained by the same general procedure as the compounds 17, 35 and 39, from the compound described as 8a in the publication and from allylamine.

The synthesis of the compounds 67, 70 and 71 is described in RIVALLE et al., *Tetrahedron* 1981; 37, 2097-2103.

The synthesis of compounds 13, 15 and 37 is described in BISAGNI et al., *Heterocycles* 1988, 27, 1671-1678.

The compound 29 is obtained by the following synthesis method: the compound described as 1a in the publication of RIVALLE et al., (*J. Med. Chem.* 1983, 26, 181-185) is suspended in DMF. Methyl iodide (10 equiv.) is added in excess. The reaction medium is heated to 80° C. for 1 h and then cooled down to room temperature. A 2M $Na_2CO_3$ solution is added and the reaction medium is brought to 80° C. for 18 hrs. The product is extracted with dichloromethane.

The compounds 72, 497 and 500 are obtained by the following synthesis method: the suitable bromopyridine (1 equivalent) and the amine (1 equivalent) are placed in tert-butanol in the presence of 2 mol % of Pd(Oac)$_2$, of 3.5 mol % of Xantphos and 2.4 equivalents of $Cs_2CO_3$. The reaction medium is brought to 90° C. for 48 hrs and is then filtered on celite and then purified on a silica column ($CH_2Cl_2$/EtOH 95:5).

For the synthesis of compound 72, 2-bromopridine and 6-amino-5,8-dimethyl-2H-isoquinolin-1-one as an amine are used. This amine is described in DUCROCQ et al., (*Tetrahedron* 1979, 35, 142).

For the synthesis of compound 497, 2-bromo-3-methoxy-pyridine and 6-amino-5,8-dimethyl-2H-isoquinolin-1-one as an amine are used.

For the synthesis of compound 500, 2-bromo-5-methylpyridine and 5,8-dimethyl-isoquinolin-6-ylamine as an amine are used. This amine is described in BALKAN et al., (*Australian Journal of Chemistry*, 1969, 22, 2489).

I-3 Constructs

The constructs β-globin Norm and Ter were obtained by PCR amplification of the constructs β-globin WT and NS39 (Thermann et al., 1998) by using the sense primer 5' GCAAC-CTCAAGCTTACACCATGGTGCACCTGAC3' (SEQ ID NO:1) and the antisense primer 5'AGAAAGCAGATCT-GCTTAGTGATACTTGTG3' (SEQ ID NO:2). The amplified fragments were cloned in the HindIII/BglII positions of a modified plasmid pRSVbgal comprising 24 MS2 sites (Fusco et al., 2003).

I-4 NMD Measurement by RT-PCR

HeLa cells were grown in 60 mm dishes in DMEM medium (Dulbecco's Modified Eagle Medium, GIBCO-BRL) supplemented with 10% (v/v) of fetal calf serum at 37° C. and with 5% $CO_2$. The cells ($1 \times 10^6$) were then transfected with 3 µg of test plasmids pmCMV-G1 (Norm or 39Ter) (Sun et al., 1998) or 3 µg pf test plasmids pmCMV-GPx1 (Norm or 46Ter) (Moriarty et al., 1998) and 1 µg of reference plasmid phCMV-MUP (Belgrader and Maquat, 1994) by using the LIPOFECTAMINE PLUS REAGENT (INVITROGEN) kit according to the instructions of the manufacturer. 24 hours after transfection, the cells were treated for 20 hours with 5 µM of each of the compounds to be tested or with 0.01% (v/v) DMSO as a control. The total RNA was purified by using TRI reagent (SIGMA-ALDRICH) according to the instructions of the manufacturer, and then reverse transcription of the mRNAs G1, GPx1 and MUP was carried out before PCR amplification, in the presence of a $^{32}$P-radiolabelled dCTP nucleotide. The PCR conditions and the analysis method were described earlier (Ishigaki et al., 2001). The PCR products were quantified on a Typhoon 9200 (Amersham Biosciences).

I-5 Translation Efficiency Test

HeLa cells were transfected with 2 µg of plasmid pFluc and 1 µg of plasmid pFluc. 24 hours after transfection, the cells were incubated in the presence of 0.01% (v/v) DMSO or of different compounds to be tested (5 µM) for 20 hours or of 100 µg/mL of cycloheximide for 4 hours before harvesting the cells. Luciferase activity was quantified on the equivalent of $2 \times 10^5$ cells on a microLumat LB 96P (EG&G Berthold) by using the Dual Glo Luciferase kit (Promega) according to the instructions of the manufacturer. Luciferase activity was then normalized with regard to the level of Fluc and Rluc mRNA.

I-6 Luciferase Activity for Measuring the Integrity of the siRNA Degradation Route in the Presence of NMD Inhibitory Compounds The cells were grown in 6-well plates and transfected by using the Lipofectamine Plus Reagent (Invitrogen) kit with 50 ng of RLperfect reporter RNA (Pillai et al., 2005), 200 ng of pG13 plasmid coding for 'Firefly luciferase' and 4 µg of pTzU6 plasmid. 24 hours after transfection, the compounds to be tested were added to the corresponding wells. 48 hours after transfection, luciferase activity was measured with the Dual Glo Luciferase kit (Promega) according to the instructions of the manufacturer.

I-7 Measurement of the Phosphorylation Level of Flag-hUPF1 by 2D Gel Analysis 293T cells ($10^6$) were transfected with 1 µg of pFLAG-hUpf1 plasmid (Sun et al., 1998) by using the Lipofectamine Plus Reagent (Invitrogen) kit according to the instructions of the manufacturer. After 12 hours, the serum was removed from the culture medium for 24 hours before adding 5 µM of compounds to be tested or, as a control, 10% (v/v) DMSO for 3 hours at 37° C. and 5% $CO_2$. Next, 10% serum is again added for 1 hour at 37° C. and 5% $CO_2$. The total proteins were purified with a lysis buffer comprising 8M urea, 2% CHAPS and 40 mM of Tris base. Migration in the first dimension was carried out according to the procedure described by AMERSHAM-BIOSCIENCES for 2D electrophoresis with an immobilized pH gradient. Immobiline™ DryStrip at pH 3-10 (18 cm) was used for separating the proteins according to their isoelectric point. Next, the second dimension was carried out by loading the first dimension on 10% SD S-PAGE gel. Finally, the proteins were transferred on a nitrocellulose membrane before incubating them with an anti-FLAG antibody (SIGMA-ALDRICH) in TBS containing 0.05% TWEEN overnight at 4° C., followed by incubation with an anti-mouse goat antibody conjugate to peroxidase (PIERCE). The proteins were then detected by using the <<SuperSignal West Femto Maximum Sensitivity Substrate>> (PIERCE).

I-8 Determination of the Step for Blocking NMD

This experiment was conducted as described earlier (Hosoda et al., 2005).

I-9 Immunofluorescence, FISH Test at Image Analysis

HeLa cells were grown on 12 mm glass slides in 10% (v/v) FBS DMEM. The cells ($10^5$) were transiently transfected with 500 ng of plasmids pGFP-GE1 (Yu et al., 2005), pYFP-hSmg5, pYFP-hSmg6, YFP-hSmg7 (Unterholzner and Izaurralde, 2004), pGFP-CCR4, pCFP-DCP 1a (Cougot et al., 2004), pCI-neo-FLAG-hUpf1 (Sun et al., 1998), pcDNA3-hUpf3a-FLAG, pcDNA3-hUpf3b-FLAG (Lykke-Andersen et al., 2000), pmCMV-G1 (Norm or 39Ter) (Sun et al., 1998) or pmCMV-GPx1 (Norm or 46Ter) (Moriarty et al., 1998). 24 hours after transfection, the cells were treated with 5 µM of compounds to be tested or 0.001% (v/v) DMSO as a control. After 20 hours, the cells were fixed by using a formalin solution (SIGMA-ALDRICH) for 10 min at room temperature and permeabilized with a 70% ethanol solution overnight at 4° C.

For the immunofluorescence tests, the fixed cells were incubated with anti-FLAG mouse antibody (SIGMA-ALDRICH) for 2 hours at room temperature, washed three times in PBS and then incubated with a mouse antibody conjugate to Cy3 or to FITC (JACKSON IMMUNORESEARCH) for one hour at room temperature. Finally, the cells were washed three times in PBS before being incubated in Hoechst (2 µg/µL) (SIGMA-ALDRICH) for 2 minutes at room temperature.

For the FISH experiments, the fixed cells are incubated in a pre-hybridization buffer (tRNA 125 µg/mL, herring DNA 500 µg/mL, BSA 1 mg/mL, dextran sulfate 0.1 g/mL, 50% formamide, 2×SSC buffer) at 37° C. for 1 hour in a tissue culture incubator. Next, the fixed cells are incubated overnight in a tissue culture incubator with the hybridization buffer (pre-hybridization buffer with probes marked with Cy3), washed three times in a SSC 2× buffer at 37° C., three times in 1×SSC buffer at room temperature, and finally incubated with Hoechst (2 ng/μL) (SIGMA-ALDRICH) for two minutes at room temperature. The probe 5'CGATCTGCGT-TCTACGGTGGT3' (SEQ ID NO:3) marked with Cy3 at the 5' and 3' ends, was used for detecting the G1 Ter or GPX1 Ter mRNAs.

The fixed cells were observed with a DMRA microscope (Leica), an oil objective PL APO 63× (NA 1.32) with A4 filters (for Hoechst), GFP and Y3 filters (for Cy3).

I-10 Immunopurification and Western Blot Analysis

Immunopurification of hUPF1 and western blot analysis were carried out according to a procedure described earlier (Lejeune and Maquat, 2004) by using an anti-hUPF1 antibody (Ohnishi et al., 2003), The western blot analyses were conducted by using a 1/250 dilution of anti-hUPF1, anti-hSMG5, anti-hSMG6 or anti-hSMG7 rabbit antibodies (Ohnishi et al., 2003), a 1/1000 dilution of anti-hUPF3/3X rabbit antibody (Ishigaki et al., 2001) or of anti-TUBILIN mouse antibody (SIGMA-ALDRICH). The proteins were detected by using the <<SuperSignal West Pico Chemiluminescent Substrate>> or <<SuperSignal West Femto Maximum Sensitivity Substrate>> (PIERCE).

II-Results

II-1 Identification of Novel NMD Inhibitors

HeLa cells were transfected with two test plasmids coding for the RNAs of β-globin (G1) and of glutathione peroxidase 1 (GPx1) and having a termination codon either premature (Ter) or not (Norm). The G1 mRNA is subject to an NMD associated with the nucleus in non-erythroid cells (Thermann et al., 1998; Zhang et al., 1998) while GPx1 mRNA is subject to cytoplasmic NMD (Moriarty et al., 1998). Further, a reference plasmid coding of mRNA of a major urinary protein (MUP) was also introduced into the cells (Ishigaki et al., 2001).

24 hours after transfection, the cells were incubated for 20 hours with DMSO (−) as a control, or with 5 μM of indole compounds shown in Table I. After 20 hours, the total RNAs are finally purified and analyzed by RT-PCR.

The results for different tested compounds are summarized in Table II.

TABLE II

| Compounds | Stabilization of the Ter G1 mRNA | Stabilization of the Ter GPx1 mRNA |
|---|---|---|
| 13 | − | − |
| 15 | − | − |
| 17 | − | − |
| 29 | − | − |
| 35 | − | − |
| 37 | − | − |
| 39 | − | − |
| 70 | +++ | ++ |
| 71 | +++ | ++ |
| 72 | +++ | ++ |
| 81 | − | − |
| 197 | +++ | ++ |
| 500 | +++ | ++ |

The results have shown that among the 30 tested compounds, five of them were able to stabilize both the Ter G1 mRNA level and the Ter GPx1 mRNA level and this in a dose-dependent way. This result was further able to be confirmed by the RPA technique. These results provide the conclusion that compounds 70, 71, 72, 497 and 500 are inhibitors of NMD and this both at the nucleus and at the cytoplasm. It should be noted that the inhibition level observed for these compounds was similar to those obtained with other NMD inhibitors such as cycloheximide or inactivation by siRNA of the expression of genes coding for hDCP2 or hPARN (Ishigaki et al., 2001; Lejeune et al., 2003) and that these compounds did not exhibit any cell toxicity under the experimental conditions (tested maximum concentration of 125 μM).

At this level, the specificity of the identified compounds was tested in different systems (absence of inhibition of splicing of introns, absence of inhibition of translation and absence of formation of stress granules) and was able to show that these compounds are novel specific NMD inhibitors.

II-2 Inhibition of NMD Upstream from hUPF1:

With the purpose of identifying the inhibition mode of the identified compounds, said compounds were tested on a system mimicking sequential recruitment of NMD factors on an mRNA (Kim et al., 2005; Lykke-Andersen et al., 2000). To do this, cells are transfected with two types of constructs one of which coded for the mRNA of Firefly Luciferase (Fluc), an mRNA containing 8 binding sites for the MS2 protein on its 3'UTR, and the second coded either for the MS2 protein or for one of the following fusion proteins: MS2-hUPF1, MS2-hTPF2 or MS2-hUPF3X. Further, HeLa cells were also transfected with a construct coding for the mRNa of Renilla Luciferase (Rluc) so as to normalize the analyzed RNA level.

The cells were then incubated for 20 hours with the compound 70 or with DMSO (−) as a negative control. The level of Rluc and Fluc mRNAs was then measured as described earlier (Hosoda et al., 2005). As a control, the expression of each of the MS2 fusion proteins was determined by a western blot.

The results have shown that in each case, the compound 70 did not affect the expression level of MS2 fusion proteins, which was never larger than the expression level of endogenous proteins. As expected and in the presence of DMSO, the expression level of Fluc mRNAs was lower in cells expressing one of the MS2-hUPF fusion proteins, as compared with cells only expressing MS2. On the other hand, the results have revealed that the compound 70 interferes with degradation induced by MS2-hUPF2 or MS2-hUPF3X, but has no effect on the degradation induced by MS2-hUPF1. It should be noted that the ratios of the Fluc/Rluc mRNAs and the inhibition level induced by the compound 70 are very similar to those observed in response to inactivation by siRNA of the expression of the gene coding for hCBP80 (Hosoda et al., 2005).

Finally, the results indicate that NMD inhibition by the compound 70 downstream from the recruitment of hUPF3X or hUPF2 and upstream from the hUPF1 functions.

II-3 The Compound 70 does not Prevent Interaction Between hUPF1 and hUPF3X:

In the light of the previous results, it was contemplated that the compound 70 would be able to prevent recruitment of hUPF1 to EJC via its interaction with other hUPF proteins. For this purpose, the hUPF1 protein was immunoprecipitated from HeLa cell extracts under conditions preserving the integrity of mRNPs (Lejeune and Maquat, 2004).

The compound 70 of DMSO(−) was added to cultures of cells 20 hours before immunoprecipitation (IP). Insofar that it was demonstrated that the hPF2 protein was not essential in certain cases of NMD (Gehring et al., 2005), the analysis was focused on the presence of the hUPF3X protein in each immunoprecipitation. As a specificity control, the absence of tubulin protein was demonstrated in each of the immunoprecipitations and a non-specific immunoprecipitation was carried out with normal rabbit serum in which no protein was detected.

The results have shown that the hUPF3X protein was present in the hUPF1 immunoprecipitations even when the cells were incubated beforehand with the compound 70.

Accordingly, the interaction between hUPF1 and hUPF3X is not abolished by the compound 70 which suggests that this compound does not inhibit recruitment of hUPF1 to EJC.

II-4 The Compound 70 Stabilizes Hyperphosphorylated Forms of hUPF1:

Insofar that hUPF1 requires a phosphorylation and dephosphorylation cycle during NMD (Ohnishi et al., 2003), the level of phosphorylation in the presence of the compound 70 was tested. For this purpose, the phosphorylation level of hUPF1 was tested in incubated cells with the compound 70 or with DMSO(−) by a 2D gel analysis. Insofar that the phosphorylation of hUPF1 is influenced by the serum (Pal et al., 2001), 293T cells instead of HeLa cells were used because of their capability of blocking their cell division at the same step of the cell cycle in the absence of serum. The cells were transfected by the expression vector pCI-neo-FLAG-hUpf1 (Sun et al., 1998), synchronized by the absence of serum 12 hours after transfection for 24 hours. Finally, DMSO or 5 μM of the compound 70 were added for 3 hours before adding serum for one hour.

The results have shown that without adding serum, the FLAG-hUPF1 protein migrates and only forms a single point corresponding to the non-phosphorylated protein (Pal et al., 2001). After adding serum, an intermediate phosphorylation of the FLAG-hUPF1 protein is observed, when the cells were incubated with DMSO and stabilization of additional phosphorylated isoforms of FLAG-hUPF1 is observed when the cells were incubated with the compound 70.

Accordingly, with the compound 70, it is therefore possible to stabilize hyperphosphorylated isoforms of the hUPF1 protein.

Insofar that it was suggested that the protein hUPF1 would be localized at the P-bodies when it is hyperphosphorylated (Unterholzner and Izaurralde, 2004), cell localization of the FLAG-hUPF1 protein in HeLa cells was tested in the presence and in the absence of compound 70.

The results show that exogenous hUPF1 protein is equally distributed in the cytoplasm when the cells have been incubated with DMSO, as this was demonstrated earlier for non-treated cells (Mendell et al., 2002), except in experiments of co-expression with hSMG7 protein, which induces recruitment of the hUPF1 protein at the P-bodies (Unterholzner and Izaurralde, 2004). On the other hand, and when the cells have been treated before hand with compound 70, cytoplasmic concentrations of FLAG-hUPF1 are observed in structures which co-localize the GFP-GE1, UFP-hSMG7, or CFP-hDCP1a, which are common markers of the P-bodies.

Accordingly, the compound 70 induces accumulation of hyperphosphorylated isoforms of hUPF1 at the P-bodies either by stimulation of phosphorylation or by inhibition of dephosphorylation.

In order to determine which of both mechanisms would be induced by the identified compounds, a complementary analysis of the immunoprecipitates of the hUPF1 protein from HeLa cells, either incubated or not in the presence of the compound 70, was carried out.

In a first phase, the analysis of hUPF1 with its dephosphorylation complex was carried out. The results have shown that hSMG5, hSMG6 and hSMG7 may be detected in cells treated with DMSO but that hSMG5 was undetectable on the other hand when the HeLa cells had been incubated beforehand with compound 70.

Accordingly, the results show that the compound 70 destabilizes the interaction between hUPFl1 and hSMG5. Finally, the presence of hSMG1 and hUPF3X in immunoprecipitations carried out on cells either incubated or not with compound 70, strongly suggests that the identified compounds have no influence on the interaction between hUPF1 and its phosphorylation complex (FIG. 3A). The obtained results defend the fact that the observed hUPF1 hyperphosphorylation state would be related to a lack of dephosphorylation, notably in the absence of interaction between hUPF1 and hSMG5, rather than to an activation of phosphorylation. Finally, this conclusion is in agreement with the identification of hSMG5 as an essential component for dephosphorylation of hUPF1 (Ohnishi et al., 2003).

II-5 hSMG5 is Excluded from P-Bodies in the Presence of the Compound 70:

It is known that hSMG5 and hSMG7 are localized in the cytoplasm and more specifically at the P-bodies (Unterholzner and Izaurralde, 2004).

HeLa cells were transfected with the expression vectors coding for YFP-hSMG5, YFP-hSMG6 or YFP-hSMG7 ((Unterholzner and Izaurralde, 2004) and CFP-hDCP1a as a marker of P-bodies. After 24 hours, the cells were incubated in the presence of DMSO or of 5 μM of compound 70.

As this was demonstrated earlier, in the absence of inhibitors, YFP-hSMG5, YFP-hSMG6 and YFP-hSMG7 are concentrated in cytoplasmic foci (Fukuhara et al., 2005; Unterholzner and Izaurralde, 2004), which foci were identified as being in majority P-bodies when CFP-DCP1a is used as a marker of P-bodies.

In the presence of the compound 70, the cytoplasmic foci containing YFP-hSMG6 or YFP-hSMG7 co-localize with the marker of the P-bodies, CFP-DCP1a. On the other hand, hSMG5 is no longer observed in cytoplasmic foci, but has a wide cytoplasmic distribution in cells treated with compound 70.

Insofar that it was demonstrated that the compound 70 inhibits NMD and induces concentration of hUPF1 in the P-bodies as demonstrated with the exogenous or endogenous hUPF1 protein, the localization of the three endogenous proteins hSMG at cytoplasmic foci was tested. This localization had never been observed because of too low expression of these proteins. By treating the cells with the compound 70, obtaining a stabilization of these factors within the P-bodies was conceivable.

The results have shown that the endogenous proteins are not detected at cytoplasmic foci for cells treated with DMSO. On the other and, and when the cells are incubated with compound 70, the results have shown a concentration of hSMG6 and hSMG7 proteins at the P-bodies, while hSMG5 is not detected at the cytoplasmic foci confirming the results obtained with exogenous proteins.

Finally, the results show that the compound 70 changes the cell localization of hSMG5 by excluding it from P-bodies. This observation is consistent with the loss of interaction between UPF1 and SMG5 when the cells are incubated with compound 70.

II-6 hUPF3 and hUPF3X Localize at the P-bodies When NMD is Blocked by the Compound 70

Since certain factors of NMD, such as hUPF1, hSMG5, hSMG6 or hSMG7 are localized at the P-bodies (Unterholzner and Izaurralde, 2004), it was contemplated that other NMD factors may pass into the P-bodies at least transiently. As the compound 70 blocks NMD in a step at which hUPF1 is confined at the P-bodies, cell localization of hUPF3 and of hUPF3X in treated and non-treated cells was tested. It was demonstrated that both proteins are mainly nuclear proteins in non-treated cells (Serin et al., 2001).

HeLa cells were transfected with the expression vectors coding for hUPF3-FLAG or hUPF3X-FLAG and with one of the following markers of P-bodies: YFP-hSMG6, YFP-hSMG7, GFP-GE1 and CFP-hDCP1a. The cells were treated with DMSO or the compound 70 before conducting immunofluorescence experiments. As for the non-treated cells (Serin et al., 2001) hUPF3 or hUPF3X are essentially localized at the nucleus when the cells are incubated with DMSO(−). On the other hand, and after incubation of the cells in the presence of compound 70, the results have shown cytoplasmic localization of hUPF3 and hUPF3X with accumulations in foci corresponding to P-bodies.

II-7 The mRNAs Containing PTCs Accumulate in the P-bodies in the Presence of the Compound 70:

Insofar that the NMD factors accumulate at the P-bodies in the presence of compound 70, localization of the NMD substrates was investigated. In yeasts, it was actually recently demonstrated that when NMD factors accumulate in P-bodies, the mRNAs containing PTCs also accumulate in the P-bodies when NMD was blocked (Sheth and Parker, 2006).

HeLa cells were transfected with Ter pmCMV-G1 or Ter pmCMV-GPx1 vectors and localization of the resulting mRNAs was analyzed with the following markers of P-bodies: GFP-GE1, YFP-hSMG6, YFP-hSMG7, CFP-hDCP1, GFP-hCCR4, FLAG-hUPF1, hUPF3-FLAG and hUPF3X-FLAG.

The results have shown that in the absence of inhibitors, no mRNA containing PTCs was able to be detected, probably because of their rapid degradation by NMD. On the other hand, and after treatment with the compound 70, the mRNAs containing PTCs are stabilized and essentially detected at cytoplasmic aggregates co-localizing with each of the tested hUPF fusion proteins.

Finally, the results have shown that the mRNAs containing PTCs were present in the P-bodies or adjacent to the latter when NMD was inhibited by compound 70.

Accumulation of mRNAs containing PTCs at the P-bodies when NMD is blocked in mammal cells was also confirmed by a more resolvent approach. In the latter, the mRNAs are marked with 24 SM2 repetitions, which allow detection of unique mRNA molecules by hybridization in situ (Fusco et al., 2003).

The results have shown that in the control cells, the mRNAs containing PTCs are essentially detected at the nucleus and the detected cytoplasmic molecules do not accumulate at the P-bodies. When NMD is inhibited by the compound 70, the results have shown an accumulation of the mRNAs containing PTCs at the level of the cytoplasm and more specifically in structures co-localizing with the P-bodies Accordingly, these results confirm that the mRNAs subject to NMD accumulate at the P-bodies when their degradation is inhibited and this conclusion does not seem to be cell-specific.

Finally, the results have shown that no wild mRNA is detected in P-bodies after incubation with compound 70, which confirms a specific NMD-inhibiting function of the identified compounds rather than a general function of inhibition of mRNA degradation.

II-8 mRNA Stabilization of Dystrophin Having a Premature Stop Codon:

The gene of dystrophin consists of 79 exons, including exons 70-79 which code for a portion of the protein which is not essential for the function of this protein in the muscle.

Among patients affected with Duchenne's muscular dystrophy (DMD), there are patients which bear a non-sense mutation in one of the exons 70-79. Nevertheless, these patients do not express the dystrophin protein because of the degradation of the mRNA by NMD and this although the truncated protein is functional. Accordingly, NMD inhibition in these patients would allow the synthesis of this truncated but functional protein.

Two cell lines originating from patients affected with DMD respectively because of retention of the intron 70 which provides a stop codon and of deletion of exons 75-76 causing a shift of the reading frame and consequently the occurrence of an early stop codon activation NMD on this mRNA, have been used.

Both of these cell lines were treated for 48 hours with the compounds 70, 71 or 72, or in presence of DMSO. The RNAs were then extracted and a RT-PCR was carried out under quantitative conditions.

The results have shown stabilization of the dystrophin mRNA by about a factor 4, following treatment with the compounds 70, 71 or 72.

II-9 NMD Inhibition in vivo:

Two murine models for NMD mechanism were used for investigating the in vivo effect of compound 70. The first model is called mdx mouse. These mice bear a non-sense mutation in the exon 23 of the gene of dystrophin. This non-sense codon induces degradation of dystrophin mRNA by NMD. These mice received an injection of DMSO (50 µL), 20, 200 or 2,000 nmol of compound 70, in the muscle. After 6, 24 and 32 hours, the mice were sacrificed, the injected muscle was sampled in order to extract RNAs and proteins therefrom. The preliminary results show stabilization of dystrophin mRNA in the mice injected with compound 70 and no stabilization in mice injected with DMSO. Further, the truncated dystrophin protein is itself also detected in mice injected with compound 70 and not in mice which have received DMSO.

The second murine model which was used is defined by the presence of a non-sense mutation in the exon 3 of the gene µ of the opiate receptor (MOR). This stop codon activates NMD on this MOR mRNA. The MOR gene is only expressed in the central nervous system which makes this model a very interesting tool in order to investigate the possibility of a chemical compound crossing the blood-brain barrier. The same procedure as for the mdx mice was followed except that the injection was made subcutaneously at the neck of the mice and the brain was sampled at different phases of the experiment. Here again, the first results show stabilization of MOR mRNA in mice injected with the compound 70 and not in mice injected with DMSO alone. Western blot analysis of the MOR protein shows the presence of the truncated protein in the same mice injected with compound 70 and not in the mice having only received DMSO. These results show that the compound 70 is active in vivo and that it may cross the blood-brain barrier which makes this compound a potential therapeutic agent for diseases affecting the central nervous system and related to NMD.

III-Discussion

With this study, it was possible to demonstrate the NMD inhibitory capability of indole derivatives. These compounds act by preventing interaction between hUPF1 and hSMG5 which results in the exclusion of hSMG5 from P-bodies, and in the stabilization of hyperphosphorylated forms of hUPF1.

Finally, with the results it was possible to demonstrate that these indole derivatives are capable of inhibiting NMD in vivo and of crossing the blood-brain barrier which makes them good candidates for the treatment of many pathologies associated with NMD.

Further these compounds prove to be excellent tools for studying the mechanism of NMD through an approach which has never been possible because of the lack of tools for specifically inhibiting this process. A benefit for laboratories working on this NMD mechanism is therefore quite conceivable.

REFERENCES

Balkan, F.; Elmes, B. C.; Loder, J. W. *Australian Journal of Chemistry* 1969, 22, 2489.

Bashkirov, V. I., H. Scherthan, J. A. Solinger, J. M. Buerstedde, and W. D. Heyer. 1997. A mouse cytoplasmic exoribonuclease (mXRN1p) with preference for G4 tetraplex substrates. *J Cell Biol.* 136:761-73.

Belgrader, P., and L. E. Maquat. 1994. Nonsense but not missense mutations can decrease the abundance of nuclear mRNA for the mouse major urinary protein, while both types of mutations can facilitate exon skipping. *Mol Cell Biol.* 14:6326-36.

Brengues, M., D. Teixeira, and R Parker. 2005. Movement of eukaryotic mRNAs between polysomes and cytoplasmic processing bodies. *Science.* 310:486-9.

Bisagni, E., Rautureau, M., Huel, C. *Heterocycles* 1988, 27, 1671-1678

Chen, C. Y., and A. B. Shyu. 2003. Rapid deadenylation triggered by a nonsense codon precedes decay of the RNA body in a mammalian cytoplasmic nonsense-mediated decay pathway. *Mol Cell Biol.* 23:4805-13.

Chin, S. Y., G. Serin, O. Ohara, and L. E. Maquat. 2003. Characterization of human Smg5/7a: a protein with similarities to *Caenorhabditis elegans* SMG5 and SMG7 that functions in the dephosphorylation of Upf1. *Rna.* 9:77-87.

Conti, E., and E. Izaurralde. 2005. Nonsense-mediated mRNA decay: molecular insights and mechanistic variations across species. *Curr Opin Cell Biol.* 17:316-25.

Cougot, N., S. Babajko, and B. Seraphim 2004. Cytoplasmic foci are sites of mRNA decay in human cells. *J Cell Biol.* 165:31-40.

Couttet, P., and T. Grange. 2004. Premature termination codons enhance mRNA decapping in human cells. *Nucleic Acids Res.* 32:488-94.

Czaplinski, K., M. J. Ruiz-Echevarria, S. V. Paushkin, X. Han, Y. Weng, H. A. Perlick, H. C. Dietz, M. D. Ter-Avanesyan, and S. W. Peltz. 1998. The surveillance complex interacts with the translation release factors to enhance termination and degrade aberrant mRNAs. *Genes Dev.* 12:1665-77.

Ducrocq, C., Bisagni, E., Rivalle. C., Lhoste, J. M. *Tetrahedron* 1979, 35, 142

Fenger-Gron, M., C. Fillman, B. Norrild, and J. Lykke-Andersen. 2005. Multiple processing body factors and the ARE binding protein TTP activate mRNA decapping. *Mol Cell.* 20:905-15.

Fukuhara, N., J. Ebert, L. Unterholzner, D. Lindner, E. Izaurralde, and E. Conti. 2005. SMG7 is a 14-3-3-like adaptor in the nonsense-mediated mRNA decay pathway. *Mol Cell.* 17:537-47.

Fusco, D., N. Accornero, B. Lavoie, S. M. Shenoy, J. M. Blanchard, R. H. Singer, and E. Bertrand. 2003. Single mRNA molecules demonstrate probabilistic movement in living mammalian cells. *Curr Biol.* 13:161-7.

Frischmeyer, P. A. and Dietz, H. C. 1999. Nonsense-mediated mRNA decay in health and disease. *Human Molecular Genetics,* 8(10):1893-1900.

Gehring, N. H., J. B. Kunz, G. Neu-Yilik, S. Breit, M. H. Viegas, M. W. Hentze, and A. E. Kulozik. 2005. Exon-junction complex components specify distinct routes of nonsense-mediated mRNA decay with differential cofactor requirements. *Mol Cell.* 20:65-75.

He, F., X. Li, P. Spatrick, R. Casillo, S. Dong, and A. Jacobson. 2003. Genomewide analysis of mRNAs regulated by the nonsense-mediated and 5' to 3' mRNA decay pathways in yeast. *Mol Cell.* 12:1439-52.

Hosoda, N., Y. K. Kim, F. Lejeune, and L. E. Maquat. 2005, CBP80 promotes interaction of Upf1 with Upf2 during nonsense-mediated mRNA decay in mammalian cells. *Nat Struct Mol Biol.* 12:893-901.

Ingelfinger, D., D. J. Amdt-Jovin, R. Lulumann, and T. Acbsel. 2002. The human LSm1-7 proteins colocalize with the mRNA-degrading enzymes Dcp1/2 and XmI in distinct cytoplasmic foci. *Rna.* 8:1489-501.

Ishigaki, Y., X. Li, G. Serin, and L. E. Maquat. 2001. Evidence for a pioneer round of mRNA translation: mRNAs subject to nonsense-mediated decay in mammalian cells are bound by CBP80 and CBP20. *Cell.* 106:607-17.

Kashima, I., A. Yamashita, N. Izumi, N. Kataoka, R. Morishita, S. Hoshino, M. Ohno, G. Dreyfuss, and S. Ohno. 2006. Binding of a novel SMG-1-Upf1-eRF1-eRF3 complex (SURF) to the exon junction complex triggers Upf1 phosphorylation and nonsense-mediated mRNA decay. *Genes Dev.* 20:35567.

Kedersha, N., G. Stoecklin, M. Ayodele, P. Yacono, J. Lykke-Andersen, M. J. Fitzler, D. Schemer, R. J. Kaufman, D. E. Golan, and P. Anderson. 2005. Stress granules and processing bodies are dynamically linked sites of mRNP remodeling. *J. Cell Biol.* 169:871-84.

Kim, Y. K., L. Furic, L. Desgroseillers, and L. E. Maquat. 2005. Mammalian Staufenl recruits Upf1 to specific mRNA 3'UTRs so as to elicit mRNA decay. *Cell.* 120:195-208.

Kuzmiak, H. A., and L. E. Maquat. 2006. Applying nonsense-mediated mRNA decay research to the clinic: progress and challenges. *Trends Mol Med.*

Lejeune, F., X. Li, and L. E. Maquat. 2003. Nonsense-mediated mRNA decay in mammalian cells involves decapping, deadenylating, and exonucleolytic activities. *Mol Cell.* 12:675-87.

Lejeune, F., and L. E. Maquat. 2004. Immunopurification and analysis of protein and RNA components of mRNP in mammalian cells. *Methods Mol Biol.* 257:115-24.

Lejeune, F., and L. E. Maquat. 2005. Mechanistic links between nonsense-mediated mRNA decay and pre-mRNA splicing in mammalian cells. *Curr Opin Cell Biol.* 17:309-15.

Lykke-Andersen, J., M. D. Shu, and J. A. Steitz. 2000. Human Upf proteins target an mRNA for nonsense-mediated decay when bound downstream of a termination codon. *Cell.* 103:1121-31.

Maquat, L. E. 2004a. Nonsense-Mediated mRNA Decay: A Comparative Analysis of Different Species. *Current Genomics.* 5:175-190.

Maquat, L. E. 2004b. Nonsense-mediated mRNA decay: splicing, translation and mRNP dynamics. *Nat Rev Mol Cell Biol.* 5:89-99.

Mendell, J. T., C. M. ap Rhys, and H. C. Dietz. 2002. Separable roles for rent1/hUpf1 in altered splicing and decay of nonsense transcripts. *Science.* 298:419-22.

Mendell, J. T., N. A. Sharifi, J. L. Meyers, F. Martinez-Murillo, and H. C. Dietz. 2004. Nonsense surveillance regulates expression of diverse classes of mammalian transcripts and mutes genomic noise. *Nat Genet.* 36:1073-8.

Moriarty, P. M., C. C. Reddy, and L. E. Maquat. 1998. Selenium deficiency reduces the abundance of mRNA for Se-dependent glutathione peroxidase 1 by a UGA-dependent mechanism likely to be nonsense codon-mediated decay of cytoplasmic mRNA. *Mol Cell Biol.* 18:2932-9.

Ohnishi, T., A. Yamashita, 1. Kashima, T. Schell, K. R. Anders, A. Grimson, T. Hachiya, M. W. Hentze, P. Anderson, and S. Ohno. 2003. Phosphorylation of hUPF1 induces formation of mRNA surveillance complexes containing hSMG-5 and hSMG-7. *Mol Cell.* 12:1187-200.

Page, M. F., B. Carr, K. R. Anders, A. Grimson, and P. Anderson. 1999. SMG-2 is a phosphorylated protein required for mRNA surveillance in *Caenorhabditis elegans* and related to Upf1p of yeast. *Mol Cell Biol.* 19:5943-51.

Pal, M., Y. Ishigaki, E. Nagy, and L. E. Maquat. 2001. Evidence that phosphorylation of human Upf1 protein varies with intracellular location and is mediated by a wortmannin-sensitive and rapamycin-sensitive PI 3-kinase-related kinase signaling pathway. *Rna.* 7:5-15.

Pillai, R. S., S. N. Bhattacharyya, C. G. Artus, T. Zoller, N. Cougot, E. Basyuk, E. Bertrand, and W. Filipowicz. 2005. Inhibition of translational initiation by Let-7 MicroRNA in human cells. *Science.* 309:1573-6.

Rehwinkel, J., I. Letunic, J. Raes, P. Bork, and E. Izaurralde. 2005. Nonsensemediated mRNA decay factors act in concert to regulate common mRNA targets. *Rna.* 11:1530-44.

Rivalle, C., Ducrocq, C., Lhoste, J. M., Wendling, F., Bisagnie, E., Chermann, J. C. T *Tetrahedron* 1981; 37, 2097-2103

Rivalle, C., Wendling, F., Tambourin, P., Lhoste, J. M., Bisagni, E. *J. Med. Chem.* 1983, 26, 181-185Serin, G., A. Gersappe, J. D. Black, R. Aronoff, and L. E. Maquat. 2001. Identification and characterization of human orthologues to *Saccharomyces cerevisiae* Upf2 protein and Upf3 protein (*Caenorhabditis elegans* SMG-4). *Mol Cell Biol.* 21; 209-23.

Sheth, U., and R. Parker. 2003. Decapping and decay of messenger RNA occur in cytoplasmic processing bodies. *Science.* 300:805-8.

Sheth, U., and R. Parker. 2006. Targeting of aberrant mRNAs to cytoplasmic processing bodies. *Cell.* 125:1095-109.

Soret, J., N. Bakkour, S. Maire, S. Durand, L. Zekri, M. Gabut, W. Fic, G. Divita, C. Rivalle, D. Dauzonne, C. H. Nguyen, P. Jeanteur, and J. Tazi. 2005. Selective modification of alternative splicing by indole derivatives that target serine-arginine-rich protein splicing factors. *Proc Natl Acad Sci USA.* 102:8764-9.

Sun, X., H. A. Perlick, H. C. Dietz, and L. E. Maquat. 1998. A mutated human homologue to yeast Upf1 protein has a dominant-negative effect on the decay of nonsense-containing mRNAs in mammalian cells. *Proc Natl Acad Sci USA.* 95:10009-14.

Sureau, A., R. Gattoni, Y. Dooghe, J. Stevenin, and J. Soret. 2001. SC35 autoregulates its expression by promoting splicing events that destabilize its mRNAs. *Embo J.* 20:1785-96.

Teixeira, D., U. Sheth, M. A. Valencia-Sanchez, M. Brengues, and R. Parker. 2005. Processing bodies require RNA for assembly and contain nontranslating mRNAs. *Rna.* 11:371-82.

Thermann, R., G. Neu-Yilik, A. Deters, U. Frede, K. Wehr, C. Hagemeier, M. W. Hentze, and A. E. Kulozik. 1998. Binary specification of nonsense codons by splicing and cytoplasmic translation. *Embo J.* 17:3484-94.

Tourriere, H., K. Chebli, L. Zekri, B. Courselaud, J. M. Blanchard, E. Bertrand, and J. Tazi. 2003. The RasGAP-associated endoribonuclease G3BP assembles stress granules. *J Cell Biol.* 160:823-31.

Unterholzner, L., and E. Izaurralde. 2004. SMG7 acts as a molecular link between mRNA surveillance and mRNA decay. *Mol Cell.* 16:587-96.

van Dijk, E., N. Cougot, S. Meyer, S. Babajko, E. Wahle, and B. Seraphin. 2002. Human Dcp2: a catalytically active mRNA decapping enzyme located in specific cytoplasmic structures. *Embo J.* 21:6915-24.

Wollerton, M. C., C. Gooding, E. J. Wagner, M. A. Garcia-Blanco, and C. W. Smith. 2004. Autoregulation of polypyrimidine tract binding protein by alternative splicing leading to nonsense-mediated decay. *Mol Cell.* 13:91-100.

Yamashita, A., T. Ohnishi, I. Kashima, Y. Taya, and S. Ohno. 2001. Human SMG-1, a novel phosphatidylinositol 3-kinase-related protein kinase, associates with components of the mRNA surveillance complex and is involved in the regulation of nonsense-mediated mRNA decay. *Genes Dev.* 15:2215-28.

Yu, J. H., W. H. Yang, T. Gulick, K. D. Bloch, and D. B. Bloch. 2005. Ge-1 is a central component of the mammalian cytoplasmic mRNA processing body. *Rna.* 11:1795-802.

Zhang, J., X. Sun, Y. Qian, and L. E. Maquat, 1998. Intron function in the nonsense-mediated decay of beta-globin mRNA: indications that pre-mRNA splicing in the nucleus can influence mRNA translation in the cytoplasm. *Rna.* 4:801-15.

---

The invention claimed is:

1. A compound corresponding to the following formula II:

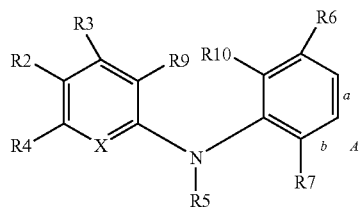

wherein:

X represents N or the anhydrobase N⁺R8, wherein R8 represents a hydrogen atom, a hydroxyl or alkyl or methoxy group optionally substituted with a phenyl group, R2, R3, and R4 independently represent a hydrogen atom or a halogen atom or an optionally substituted alkyl, amino group, alkene, ester, sulfonamide, ether, or benzyl group, R5 represents a hydrogen atom or an optionally substituted, saturated or unsaturated alkyl group, amino group, or benzyl group, R6 represents an optionally substituted C1-C3 alkyl group, R7 represents a hydrogen atom or an optionally substituted C1-C3 alkyl group, and R7 is absent when A is in position b, and R9 and R10 independently represent a hydrogen atom, a R11, OR11, or SR11 group, wherein R11 independently represents a hydrogen atom, an optionally substituted, saturated or unsaturated, C1-C3 alkyl group, which may contain one or more sulfur, oxygen, or nitrogen atoms; and A represents a ring group which, when A is in the a or b position, corresponds to:

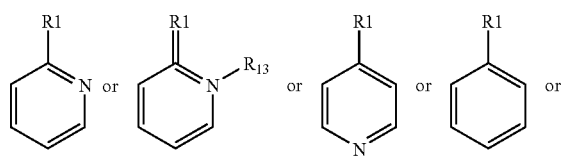

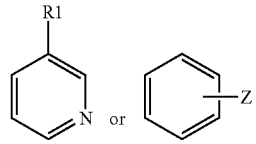

wherein:
R1 represents a hydrogen, oxygen, or halogen atom, or an optionally substituted, linear or branched and/or unsaturated alkyl group,
R13 represents a hydrogen atom or C1-C4 alkyl group optionally substituted, and
Z represents a R1 group;
pharmaceutically acceptable salts of said compounds, their isomers and/or a mixture thereof.

2. The compound according to claim 1, of the following formula Ia:

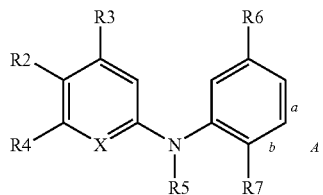

Formula Ia wherein R2, R3, R4, R5, R6, R7, X, and the ring A are as defined in claim 1.

3. The compound according to claim 1, wherein R2, R3, and R4 represent independently of each other, a hydrogen atom or a halogen atom or an optionally substituted alkyl, amino, alkene, or benzyl group.

4. The compound according to claim 1, wherein R2, R3, and R4 represent independently of each other, a hydrogen atom or a halogen atom or a C1-C4 alkyl group.

5. The compound according to claim 4, wherein R2, R3, and/or R4 represent independently of each other, a halogen atom selected from the group consisting of F, Cl, Br, and I.

6. The compound according to claim 1, wherein R5 represents a hydrogen atom or a saturated or unsaturated alkyl group.

7. The compound according to claim 1, wherein R7 represents a methyl or ethyl group.

8. The compound according to claim 1, wherein R1 represents a hydrogen, oxygen, or halogen atom.

9. The compound according to claim 1, wherein the ring A is in position a.

10. The compound according to claim 1, wherein the ring A represents:

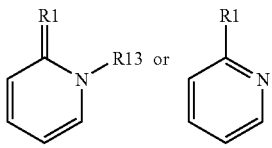

wherein R1 and R13 are as defined in claim 1.

11. The compound according to claim 10, wherein A is selected from the group consisting of:

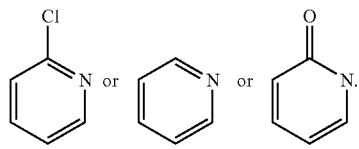

12. The compound according to claim 1, wherein the compound is selected from the group consisting of:
    5,8-dimethyl-6-(pyridin-2-ylamino)-2H-isoquinolin-1-one;
    5,8-dimethyl-6-(3-methoxy-pyridin-2-ylamino)-isoquinolin-1-one; and
    5,8-dimethyl-6-(5-methyl-pyridin-2-ylamino)-isoquinoline.

13. The compound according to claim 12, wherein the compound is 5,8-dimethyl-6-(pyridin-2-ylamino)-2H-isoquinolin-1-one.

14. A pharmaceutical composition comprising at least one indole derivative according to claim 1 and optionally a pharmaceutically acceptable support.

15. A method for treating Duchenne's muscular dystrophy (DMD) comprising the administration of an effective amount of a compound of claim 1.

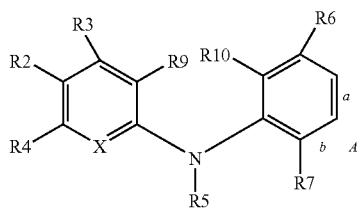

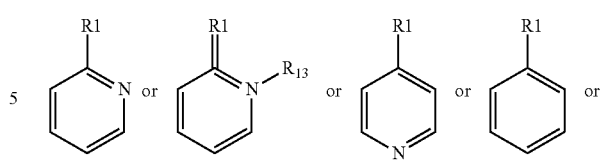

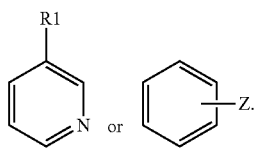

16. The method according to claim 15, wherein said compound corresponds to the following formula I:

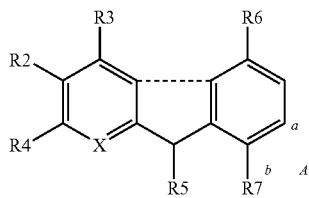

wherein:
    R2, R3, R4, R5, R6, R7, X, and the ring A are as defined in claim 1.

17. The method according to claim 15, wherein R9 and R10 both represent a hydrogen atom.

18. The method according to claim 15, wherein the ring A is in the a position.

19. The method according to claim 15, wherein the compound is selected from the group consisting of:
    5,8-dimethyl-6-(pyridin-2-ylamino)-2H-isoquinolin-1-one;
    5,8-dimethyl-6-(3-methoxy-pyridin-2-ylamino)-isoquinolin-1-one; and
    5,8-dimethyl-6-(5-methyl-pyridin-2-ylamino)-isoquinoline.

* * * * *

SEQUENCE LISTING

```
<160> NUMBER OF SEQ ID NOS: 3

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcaacctcaa gcttacacca tggtgcacct gac                                    33

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 2
agaaagcaga tctgcttagt gatacttgtg                                  30

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
cgatctgcgt tctacggtgg t                                           21
```